United States Patent
Gindele et al.

(10) Patent No.: US 9,889,292 B2
(45) Date of Patent: Feb. 13, 2018

(54) DEPLOYABLE ELECTRODE LEAD ANCHOR

(71) Applicant: Boston Scientific Scimed, Inc., Maple Grove, MN (US)

(72) Inventors: Paul J. Gindele, Buffalo, MN (US); Shiva Moosai, New Hope, MN (US); John Jason Buysman, Minnetonka, MN (US); Karen Pilney Montpetit, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/219,521

(22) Filed: Jul. 26, 2016

(65) Prior Publication Data

US 2016/0331957 A1 Nov. 17, 2016

Related U.S. Application Data

(60) Division of application No. 13/167,541, filed on Jun. 23, 2011, now Pat. No. 9,427,573, which is a continuation-in-part of application No. 12/558,143, filed on Sep. 11, 2009, now abandoned, which is a continuation-in-part of application No. 12/170,582, filed on Jul. 10, 2008, now abandoned.

(60) Provisional application No. 61/358,053, filed on Jun. 24, 2010, provisional application No. 61/360,157, filed on Jun. 30, 2010, provisional application No. 61/096,387, filed on Sep. 12, 2008, provisional application No. 61/160,765, filed on Mar. 17, 2009, provisional application No. 60/948,908, filed on Jul. 10, 2007.

(51) Int. Cl.
*A61N 1/05* (2006.01)
*A61N 1/36* (2006.01)

(52) U.S. Cl.
CPC ....... *A61N 1/0558* (2013.01); *A61N 1/36007* (2013.01); *A61N 1/3606* (2013.01)

(58) Field of Classification Search
CPC . A61N 1/0558; A61N 1/36007; A61N 1/3606
See application file for complete search history.

(56) References Cited

U.S. PATENT DOCUMENTS

| | | | | |
|---|---|---|---|---|
| 4,799,495 A | * | 1/1989 | Hawkins | A61B 17/3403 600/567 |
| 5,683,447 A | * | 11/1997 | Bush | A61N 1/056 607/126 |
| 5,728,133 A | * | 3/1998 | Kontos | A61B 17/0057 128/887 |
| 2007/0265609 A1 | * | 11/2007 | Thapliyal | A61B 18/1492 606/27 |

(Continued)

*Primary Examiner* — Rex R Holmes
(74) *Attorney, Agent, or Firm* — Brake Hughes Bellermann LLP (57) ABSTRACT

A system includes an introducer sheath having a sheath wall and a longitudinal axis, an electrode lead including a lead body and at least one electrode at a distal end of the lead body. The distal end of the lead body is received within the sheath. At least one anchor wire is within the sheath and has a proximal end attached to the distal end of the lead body. The a least one anchor wire moves through at least one opening in the sheath wall responsive to movement of the lead body relative to the introducer sheath.

12 Claims, 9 Drawing Sheets

(56) References Cited

U.S. PATENT DOCUMENTS

2007/0265675 A1* 11/2007 Lund .................. A61N 1/36007
607/41

* cited by examiner

DEPLOYABLE ELECTRODE LEAD ANCHOR

CROSS-REFERENCE TO RELATED APPLICATION

The present application is a divisional of U.S. patent application Ser. No. 13/167,541, filed Jun. 23, 2011, now U.S. Pat. No. 9,427,573, which is based on and claims the benefit of U.S. provisional patent application Ser. No. 61/358,053, filed Jun. 24, 2010, and U.S. provisional patent application Ser. No. 61/360,157, filed Jun. 30, 2010, which is a continuation-in-part of and claims priority to U.S. patent application Ser. No. 12/558,143, filed Sep. 11, 2009, which claims the benefit of U.S. provisional patent application Ser. Nos. 61/096,387 filed Sep. 12, 2008 and 61/160,765 filed Mar. 17, 2009, and is a continuation-in-part of U.S. application Ser. No. 12/170,582 filed Jul. 10, 2008, which in turn claims the benefit of U.S. provisional patent application Ser. No. 60/948,908, filed Jul. 10, 2007. The content of each of the above-referenced applications, is hereby incorporated by reference in its entirety.

FIELD

Embodiments of the invention generally relate to a deployable anchor that facilitates securing an electrode lead to internal tissue of a patient and preventing migration of the electrode lead relative to the tissue of the patient. Embodiments of the anchor may also be retracted to simplify the removal of the electrode lead from the tissue of the patient.

BACKGROUND

Implantable electronic stimulator devices, such as neuromuscular stimulation devices, have been disclosed for use in the treatment of various pelvic conditions, such as urinary incontinence, fecal incontinence and sexual dysfunction. Such devices generally include one or more electrodes that are coupled to a control unit by electrode leads. Electrical signals are applied to the desired pelvic tissue of the patient through the electrode leads in order to treat the condition of the patient. The electrode leads are typically secured to the tissue using an anchor in the form of a helical coil. Exemplary implantable electronic stimulator devices and uses of the devices are disclosed in U.S. Pat. Nos. 6,354,991, 6,652,449, 6,712,772 and 6,862,480, each of which is hereby incorporated by reference in its entirety.

An anchor is typically attached to the distal end of the electrode lead to secure the electrode lead within tissue of the patient and prevent relative movement between the anchor and the tissue in which the anchor in embedded.

SUMMARY

Some embodiments of the invention are directed to an electrode lead comprising a lead body, at least one electrode at a distal end of the lead body, an actuatable member and at least one anchor wire. The actuatable member is positioned within a lumen of the lead body. The at least one anchor wire has a proximal end that is attached to the actuatable member. Movement of the actuatable member relative to the lead body moves the at least one anchor wire through at least one opening in the lead body.

Another embodiment is directed to a system that comprises an introducer sheath, an electrode lead and at least one anchor wire. The introducer sheath has a sheath wall and a longitudinal axis. The electrode lead comprises a lead body and at least one electrode at a distal end of the lead body. The distal end of a lead body is received within the sheath. The at least one anchor wire has a proximal end that is attached to the distal end of the lead body. The at least one anchor wire moves through at least one opening in the sheath wall responsive to movement of the lead body relative to the introducer sheath.

Yet another embodiment is directed to a method. In the method, an electrode lead is provided. In on embodiment, the electrode lead comprises a lead body, at least one electrode at a distal end of lead body and at least one anchor wire having a proximal end connected to the lead body. The distal end of the lead body is positioned within tissue of a patient. The distal end of the at least one anchor wire is moved radially from the lead body and into the tissue to anchor the distal end of the lead body to the tissue.

This Summary is provided to introduce a selection of concepts in a simplified form that are further described below in the Detailed Description. This Summary is not indented to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Embodiments of the invention are directed to an anchor that facilitates securing an electrode lead to internal tissue of a patient to prevent migration of the electrode lead from its intended position. The tissue in which the anchors of the present invention may be used includes adipose tissue, muscle tissue or any other tissue of the patient. In one embodiment, the tissue is located in the pelvic region of the patient. In some embodiments, the tissue, in which the anchor is to be embedded, is targeted for electrical stimulation or is adjacent a desired stimulation target site. Embodiments of the invention comprise the individual embodiments described below and combinations of two or more of the embodiments described below. Elements having the same or similar labels correspond to the same or similar elements.

Figure 1:
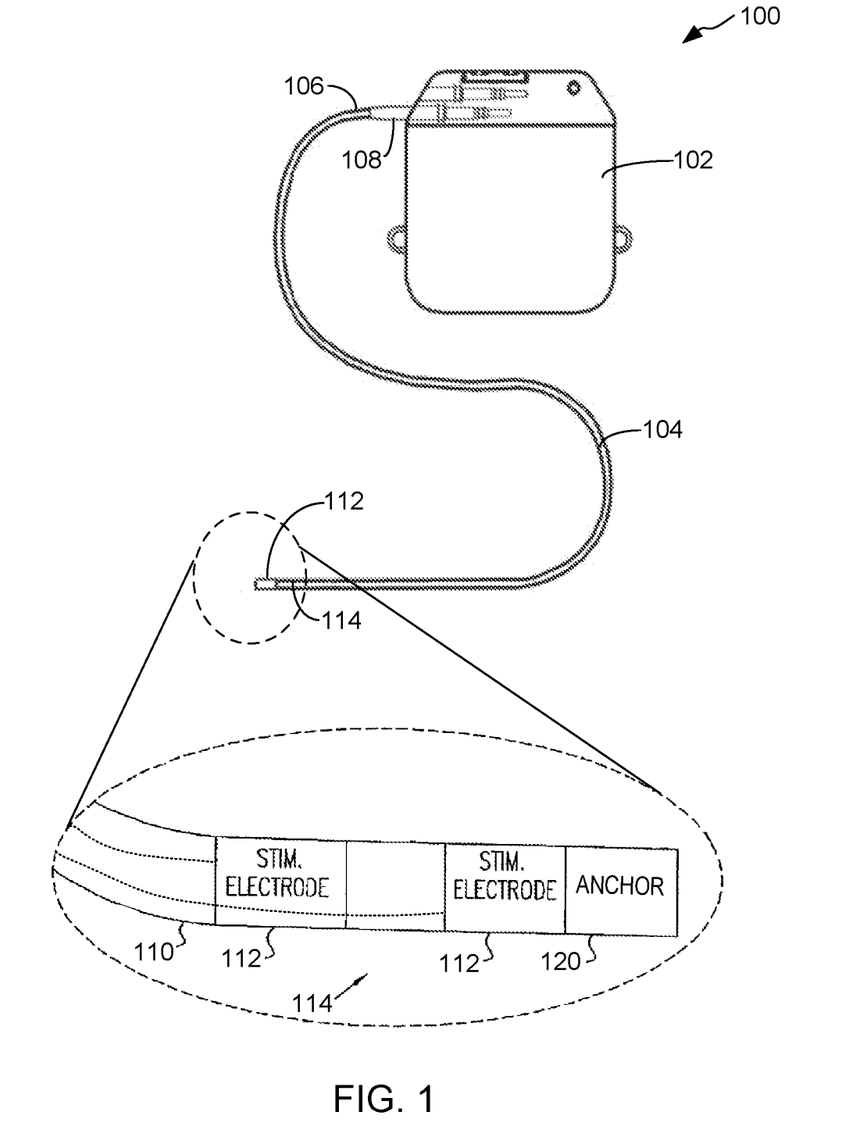
FIG. 1 is a side plan view of an exemplary electronic stimulator device, in accordance with the embodiments of the invention.

FIG. 1 is a side plan view of an exemplary electronic stimulator system 100, with which embodiments of the anchors of the present invention may be used. System 100 is configured for implantation into a pelvic region of a patient to provide muscle and/or nerve stimulation that is used to control and/or treat a pelvic condition of the patient, such as pelvic pain, urinary incontinence, fecal incontinence, erectile dysfunction or other pelvic condition that may be treated through electrical stimulation.

In one embodiment, the system 100 comprises a control unit 102 and one or more electrode leads 104, a proximal end 106 of which is coupled to the control unit 102 via a connector 108. Each electrode lead 104 comprises a lead body 110 and one or more stimulating electrodes 112 at a distal end 114 of the electrode lead 104 or lead body 110. The lead body 110 insulates electrical wires connecting the control unit 102 to the stimulating electrodes 112. The lead body 110 can be in the form of an insulating jacket typically comprising silicone, polyurethane or other flexible, biocompatible electrically insulating material. Additional electrode leads 104 or physiological sensors may be coupled to the control unit 102.

In one embodiment, the control unit 102 comprises circuitry for processing electrical signals received from the one or more stimulating electrodes 112 or physiological sensors. The control unit 102 is also configured to apply an electrical current or waveform to the tissue of the patient that is in contact with the one or more stimulating electrodes 112.

The electrode lead 104 can be anchored to pelvic tissue of the patient (e.g., internal urinary sphincter muscle) by means of a tissue anchor 120, which is formed in accordance with embodiments of the invention described below. The anchor 120 operates to secure the position of the distal end 114 of the electrode lead 104 in the desired tissue of the patient. In one embodiment, the anchor 120 is located at the distal end 114 proximate the one or more electrodes 112. While depicted as being located at the terminating side of the electrodes 112, the anchor 120 may be located between electrodes 112 or between the electrodes 112 and the proximal end 106 of the electrode lead.

Figure 2:
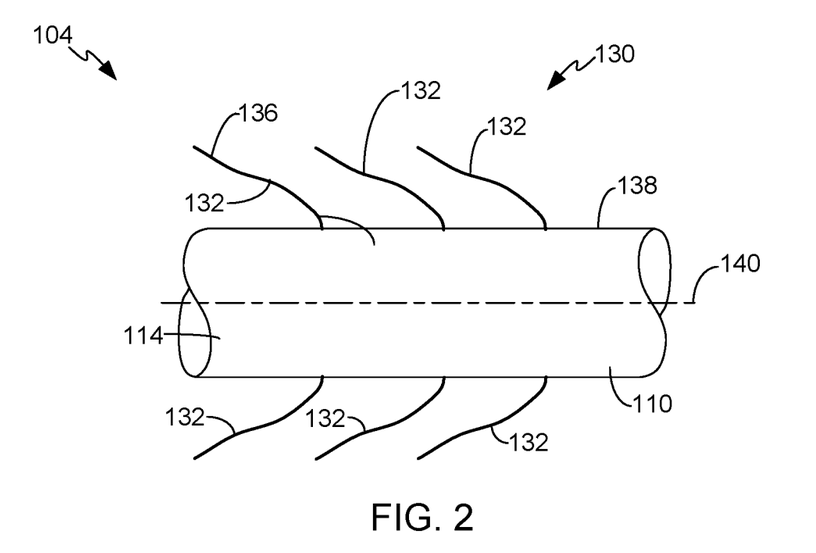
FIGS. 2 and 3 are simplified side views of a portion of an electrode lead illustrating anchors formed in accordance with embodiments of the invention.

FIG. 2 is simplified side view of a portion of a distal end 114 of electrode lead 104 that includes an anchor 130 in accordance with embodiments of the invention. The anchor 130 comprises at least one anchor wire 132 having a proximal end 134 that is attached to the lead body 110. A distal end 136 of each anchor wire 132 is configured to be fed into tissue of a patient to secure the distal end 114 of the electrode lead 104 to the tissue.

The one or more anchor wires 132 are generally formed of a suitable biocompatible material. In one embodiment, the anchor wires 132 are flexible, yet firm enough to pierce tissue of the patient upon deployment, as described below. In one embodiment, the wires 132 are formed of a memory shaped material, such as nickel titanium (i.e., NITINOL), that forces each of the anchor wires 132 to follow a desired trajectory as the wires 132 are deployed into the tissue of the patient, for example.

In one embodiment, the anchor wires 132 are attached to a sidewall 138 of the lead body 110. In one embodiment, each of the anchor wires 132 is displaced from adjacent anchor wires 132 along a longitudinal axis 140 of the lead body 110. In accordance with another embodiment, the anchor wires 132 are angularly displaced from each other about the longitudinal axis 140. For instance, the anchor wires 132 may be angularly displaced by 90 degrees from each other, as shown in FIG. 2, or other angular displacement.

Figure 3:
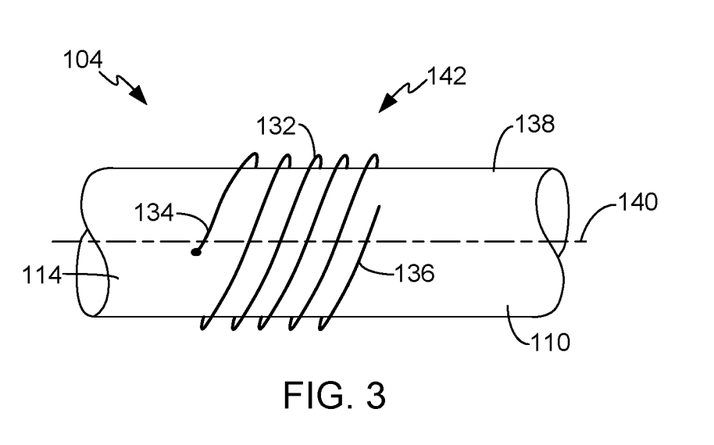

FIG. 3 is a simplified side view of a distal end 114 of an electrode lead 104 that includes an anchor 142 in accordance with embodiments of the invention. One embodiment of the anchor 142 comprises a least one anchor wire 132 having a proximal end 134 as attached to a side wall 138 of the lead body 110. In one embodiment, the anchor wire 132 is initially wrapped around the lead body 110 and the axis 140 in a coil. In one embodiment, the anchor 142 includes a plurality of anchor wires 132 that are coiled around the lead body 110. This embodiment is not illustrated in order to simplify the drawing.

Figure 4:
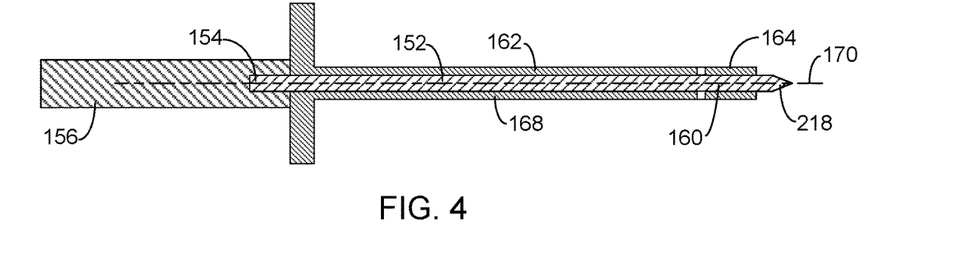
FIG. 4 is a simplified side cross-sectional view of an exemplary introducer in accordance with embodiments of the invention.

In one embodiment, the distal ends 114 of the electrode leads 104 illustrated in FIGS. 2 and 3 are configured to be deployed into tissue of a patient using an introducer. A simplified side cross-sectional view of an exemplary introducer 150 that may be used to deploy the electrode leads 104 of FIGS. 2 and 3 is provided in FIG. 4. In one embodiment, the introducer 150 is formed of biocompatible materials. A guide needle 152 having a proximal end 154 coupled to a handle 156 and a needle tip 158 at a distal end 160 may be received within an introducer sheath 162 of the introducer 150. The combination of the guide needle 152 and the introducer sheath 162 is used by the physician to create a pathway to the tissue of the patient that is targeted for electrical stimulation. Once the needle tip 158 of the guide needle 152 is positioned in or adjacent to the targeted tissue, the guide needle 152 is removed from the introducer sheath 162. This creates a pathway through the patient to the targeted tissue. The distal end 114 of the electrode lead 104 may then be inserted through the introducer sheath 162 to place the distal end 114 of the electrode lead 104 at the distal end 164 of the introducer sheath 162, in accordance with conventional techniques.

Figure 5:
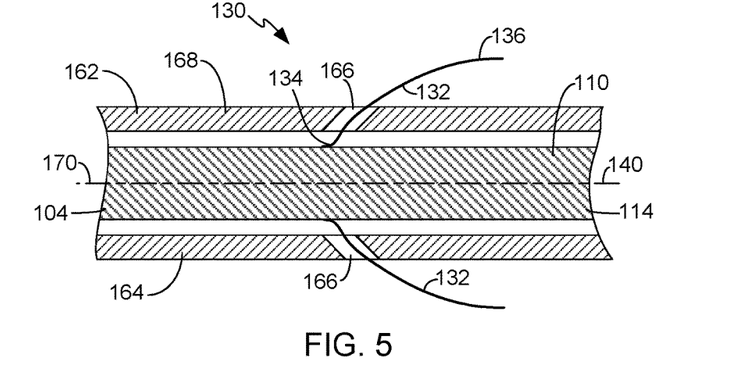
FIG. 5 is a simplified side cross-sectional view of a portion of the electrode lead of FIG. 2 within an introducer sheath.

FIG. 5 illustrates a portion of the distal end 114 of the electrode lead 104 of FIG. 2 within the distal end 164 of the introducer sheath 162. In one embodiment, the distal end 164 of the introducer sheath 162 includes at least one opening 166 in a sheath wall 168. The one or more openings 166 are configured to receive the distal ends 136 of corresponding anchor wires 132 of the anchor 130. As the distal end 114 of the electrode lead 104 is advanced toward the distal end 164 of the introducer sheath by the physician along a longitudinal axis 170 of the introducer sheath, which generally corresponds to the axis 140 of the lead body 110, the distal ends 136 of the one or more anchor wires 132 travel through to the corresponding openings 166 in the sheath wall 168, as shown in FIG. 5. Continued motion of the distal end 114 of the electrode lead 104 relative to the introducer sheath 162 causes the distal ends 136 to extend into the tissue of the patient. In one embodiment, the anchor wire 132 travels in the direction that is generally radial to the longitudinal axis 170 of the introducer sheath 162 and/or the longitudinal axis 140 of the lead body 110.

This deployment of the one or more anchor wires 132 of the anchor 130 is followed by the removal of the introducer sheath 162 in accordance with conventional techniques. For instance, the introducer sheath 162 may be split into separate halves that allow for the removal of the introducer sheath 162 without disrupting the placement of the anchor wires 132 in the tissue of the patient. The one or more anchor wires 132 that extend generally radially from the longitudinal axis 140 of the lead body 110 into the tissue of the patient operate to secure the position of the distal end 114 in the targeted tissue. The electrode lead 104 may then be used to perform electrical stimulation operations on the targeted tissue in accordance with conventional techniques.

Figure 6:
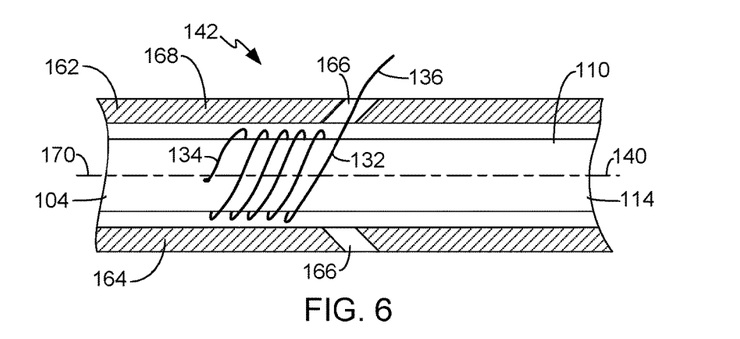
FIG. 6 is a simplified side view of a portion of the electrode lead of FIG. 3 within an introducer sheath shown in cross-section.

FIG. 6 is a simplified side view of the distal end 114 of the electrode lead 104 of FIG. 3 within the distal end 164 of the introducer sheath 162. In accordance with this embodiment, the anchor 142 is deployed by the physician rotating the lead body 110 about the longitudinal axis 170 of the introducer sheath 162, or the longitudinal axis 140 of the lead body 110, relative to the introducer sheath 162. This rotation causes the distal end 136 of the anchor wire 132 to extend through the opening 166 in the sheath wall 168 and into the tissue (not shown) of the patient. The amount of the anchor wire 132 that is fed into the tissue of the patient depends on the amount the lead body 110 is rotated about the axis 170 or the axis 140 relative to the introducer sheath 162. In one embodiment, the distal end 136 of the anchor wire 132 is deployed in a direction that is generally radial to the longitudinal axis 170 or the longitudinal axis 140, as shown in FIG. 6.

After the one or more anchor wires 132 of the anchor 142 are deployed into the tissue of the patient through the rotation of the lead body 110 relative to the introducer sheath 162, the introducer sheath 162 may be removed from the patient without disturbing the anchor wires 132, such as by splitting the introducer sheath into separate halves. The resultant position of the distal end 114 of the electrode lead 104 is in the tissue by the one or more anchor wires 132.

Figure 7:
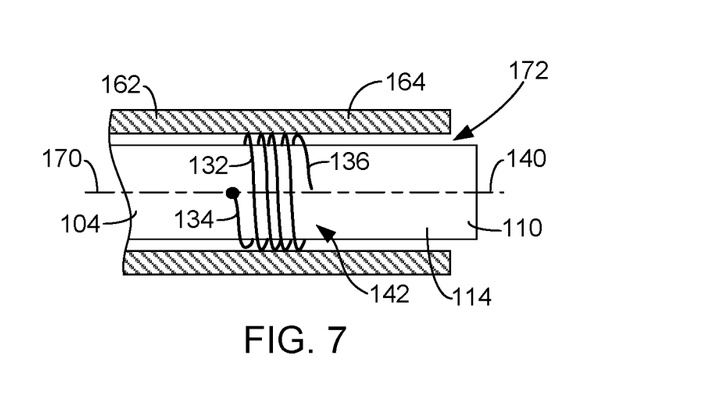
FIG. 7 is a simplified drawing of a portion of an electrode lead comprising an anchor formed in accordance with embodiments of the invention within an introducer sheath shown in cross-section.
Figure 8:
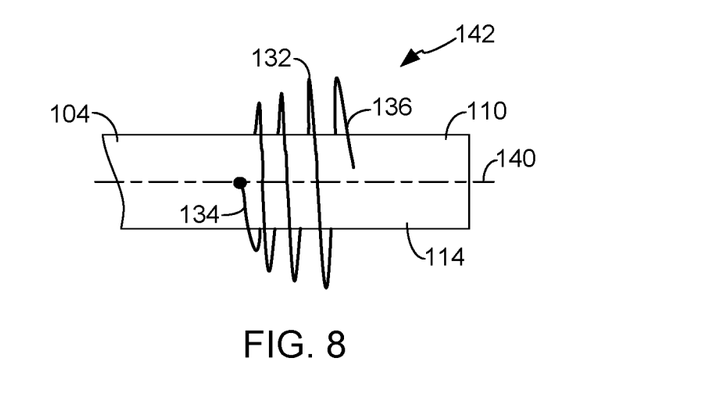
FIGS. 8 and 9 respectively show simplified side and front views of the portion of the electrode lead of FIG. 7 within tissue of a patient after the introducer sheath has been removed.
Figure 9:
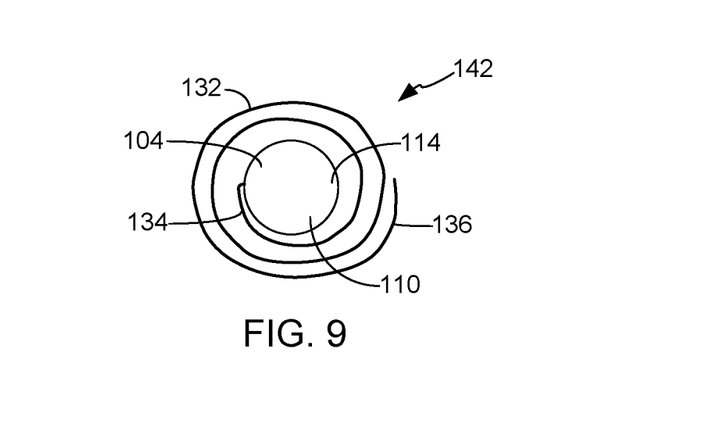

In accordance with another embodiment, the anchor 142 is wound about the distal end 114 of the electrode lead 104 such that it is radially compressed toward the longitudinal axis 140 of the lead body 110 relative to a quiescent state of the anchor wire 132. During the implantation, this radial compression of the at least one anchor wire 132 of the anchor 142 is maintained by the introducer sheath 162, as illustrated in the simplified side view of FIG. 7 with the introducer sheath 162 shown in cross-section. In accordance with this embodiment, the electrode lead 104 is either pushed through an opening 172 at the distal end 164 of the introducer sheath 162, or the introducer sheath 162 is separated into pieces and removed from the patient to expose the distal end 114 of the electrode lead 104 to the tissue of the patient. In response to the removal of the introducer sheath 162, the at least one anchor wire 132 of the anchor 142 expands radially from the longitudinal axis 140 and the lead body 110 toward an expanded quiescent state, as illustrated in the side and front views of FIGS. 8 and 9, respectively. The expansion of the at least one anchor wire 132 into the tissue of the patient secures the position of the distal end 114 of the electrode lead 104 in the tissue of the patient.

Figure 10A:
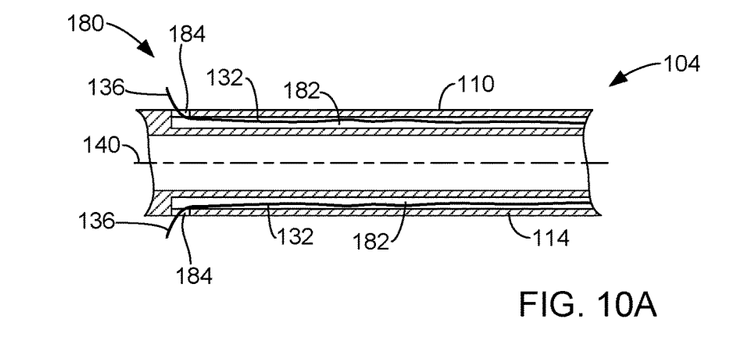
FIGS. 10A-10C are simplified side cross-sectional views of an electrode lead illustrating the deployment of an anchor in accordance with embodiments of the invention.
Figure 10B:
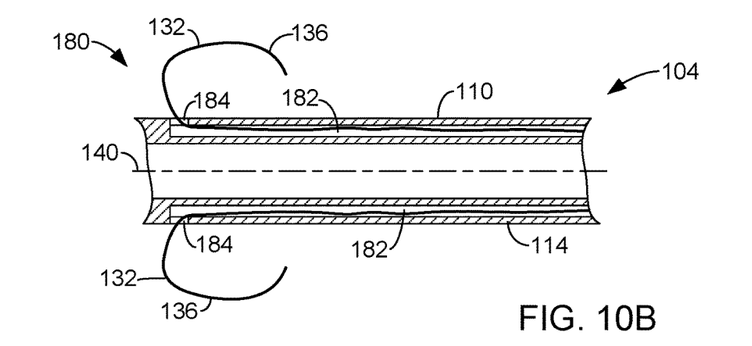
Figure 10C:
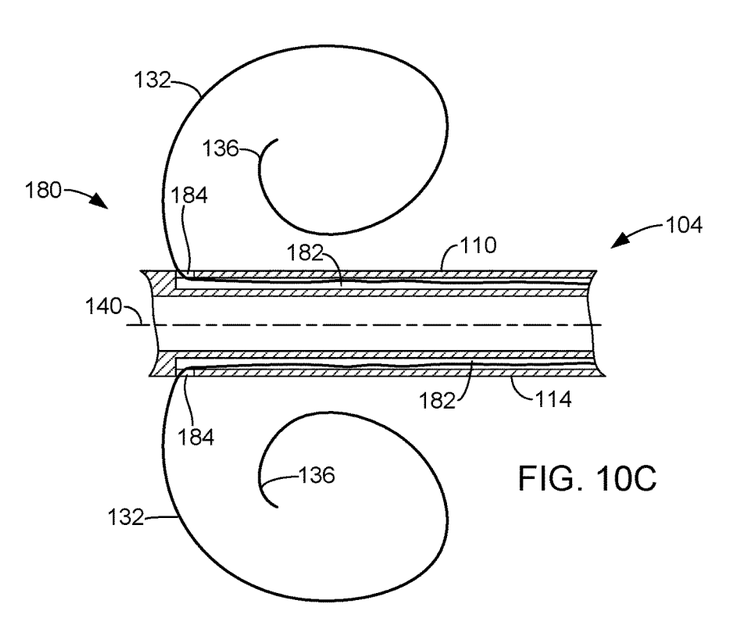

FIGS. 10A-C are side cross-sectional views of a portion of a distal end 114 of an electrode lead 104 illustrating different stages of deployment of an anchor 180 formed in accordance with embodiments of the invention. In one embodiment, the anchor 180 comprises at least one anchor wire 132 that is configured to be fed from within the anchor body 110 into the tissue of the patient after the distal end 114 of the electrode lead 104 is positioned within the targeted tissue using conventional techniques, such as those described above. In one embodiment, one or more lumens 182 are formed in the lead body 110, which guide the one or more anchor wires 132 to openings 184 formed in the lead body 110. The one or more anchor wires 132 have a retracted position, in which the distal ends 136 are contained within the corresponding lumen 182, or are only slightly extended through the openings 184, as shown in FIG. 10A. In one embodiment, the distal end 114 of the electrode lead 104 is fed, such as through an introducer, to the target tissue while the anchor 180 is in the retracted position.

Once the distal end 114 of the electrode lead 104 is positioned as desired within the targeted tissue of the patient, the one or more anchor wires 132 may be deployed from within the lumen 182 and fed into the tissue of the patient, as illustrated in FIGS. 10B and 10C. In one embodiment, the one or more anchor wires 132 are initially fed in a radial direction relative to the longitudinal axis 140 of the lead body 110. The deployment of the one or more anchor wires 132 may be accomplished by the physician using a suitable actuatable member, such as those described below, to which the proximal end of the anchor wires 132 are attached. In one embodiment, as the anchor wires 132 are fed from within the lead body 110, the one or more anchor wires 132 coil within the tissue of the patient, as shown in FIG. 10C. The deployed state (FIG. 10C) of the one or more anchor wires 132 secure the position of the distal end 114 of the electrode lead 104 in the tissue of the patient. When it is desired to remove the electrode lead 104 from the patient, the anchor wires 132 may be retracted within the lumens 182 (FIG. 10A) to reduce damage to the tissue of the patient.

Figure 11A:
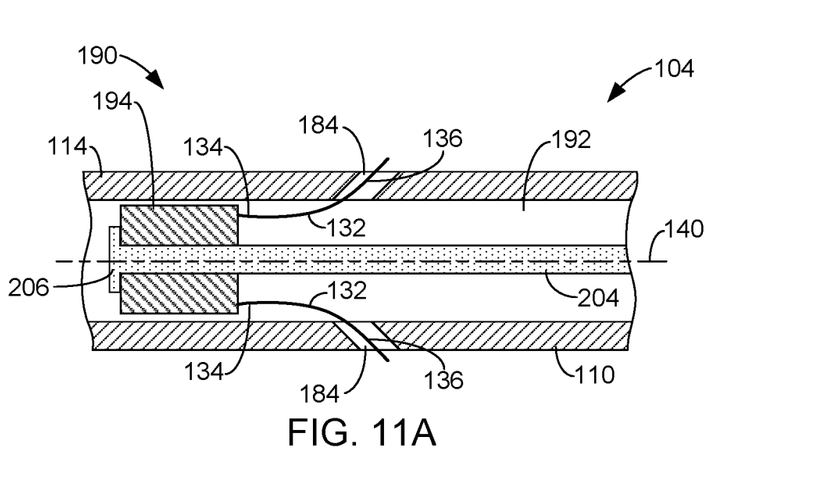
FIGS. 11A and 11B are simplified side cross-sectional views of a portion of an electrode lead illustrating the deployment of an anchor in accordance with embodiments of the invention.
Figure 11B:
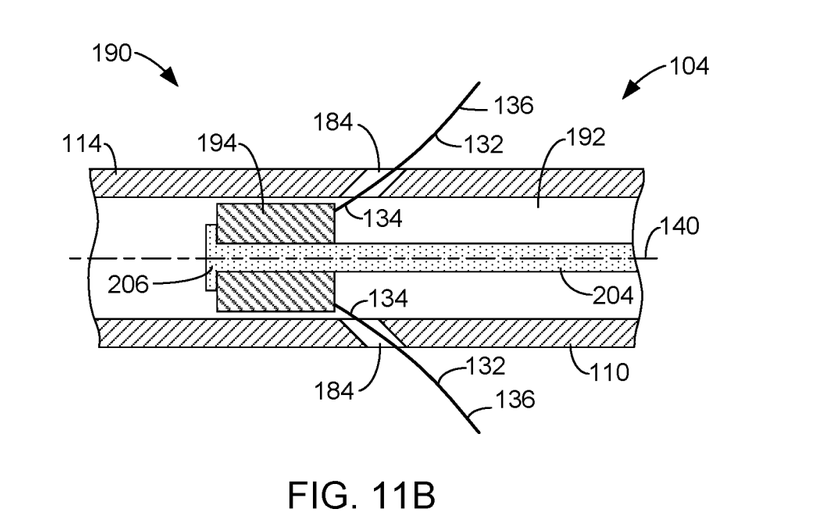

FIGS. 11A and 11B are side cross-sectional views of a portion of a distal end 114 of an electrode lead 104 that includes an anchor 190 formed in accordance with embodiments of the invention. Anchor 190 is similar to anchor 180 (FIGS. 10A-C) in that it includes one or more anchor wires 132 that may be fed from one or more lumens 192 within the anchor body 110. In one embodiment, the proximal ends 134 of the one or more anchor wires are attached to an actuatable member 194. Movement of the actuatable member 194 relative to the lead body 110 along the longitudinal axis 140 transitions the one or more anchor wires 132 between a retracted position (FIG. 11A) and an extended or deployed position (FIG. 11B). As mentioned above with regard to anchor 180, the retracted position of the anchor 190 may position the distal ends 136 of the one or more anchor wires 132 within the lumen 192, or slightly extended through the openings 184 of the lead body 110. The distal end 114 of the electrode lead 110 is positioned within the target tissue using conventional techniques while the anchor 190 is in the retracted position. Once positioned within the targeted tissue of the patient, the actuatable member 194 is moved along the longitudinal axis 140 relative to the lead body 110 to move the distal ends 136 of the one or more anchor wires 132 through the openings 184 and into the tissue of the patient, as illustrated in FIG. 11B. When it is desired to remove the electrode lead 104 from the patient, the anchor wires 132 may be retracted within the lumen 192 (FIG. 11A) to reduce damage to the tissue of the patient.

Figure 12A:
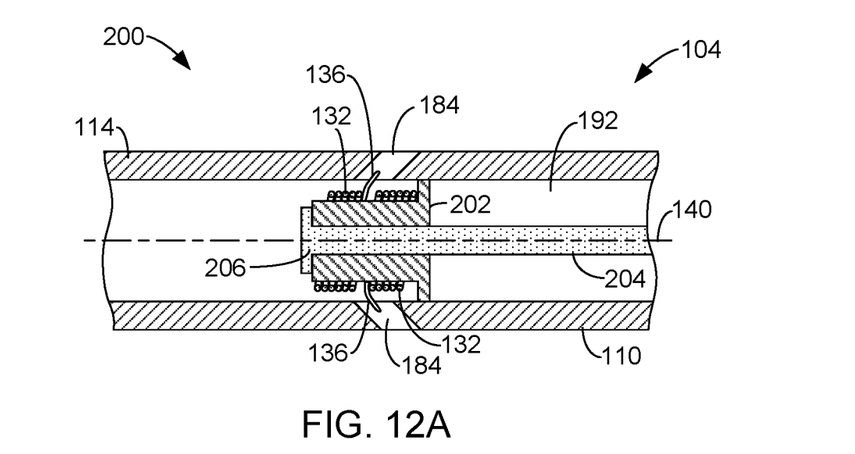
FIGS. 12A and 12B are simplified side cross-sectional views of a portion of an electrode lead illustrating the deployment of an anchor in accordance with embodiments of the invention.
Figure 12B:
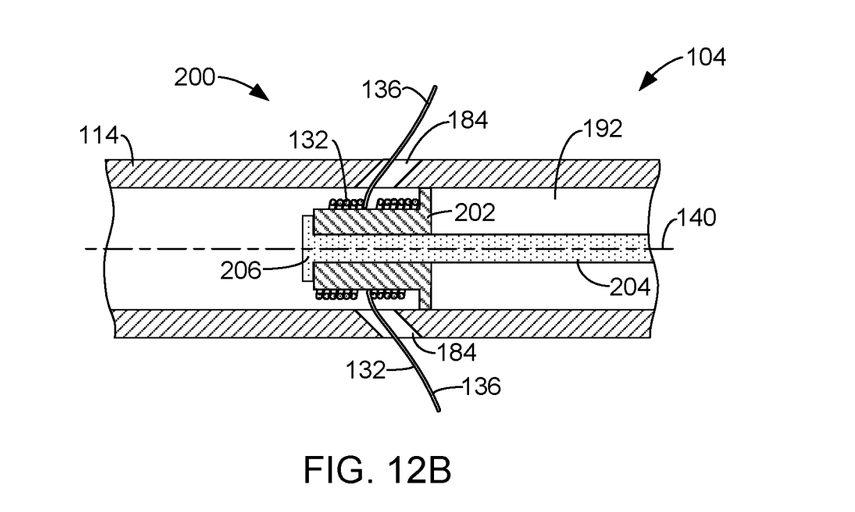

FIGS. 12A and 12B are simplified side cross-sectional views of a portion of a distal end 114 of an electrode lead 104 that includes an anchor 200 formed in accordance with embodiments of the invention. The anchor 200 includes one or more anchor wires 132 that are contained within one or more lumens 192 of the lead body 110. In one embodiment, proximal ends 134 of the one or more anchor wires 132 are attached to an actuatable member 202. Additionally, the one or more anchor wires 132 are wound around the actuatable member 202, which is configured to rotate generally about the longitudinal axis 140 of the lead body 110. Initially, the anchor 200 is placed in a retracted state, in which the distal ends 136 of the one or more anchor wires 132 are located within the lumen 192 or openings 184 of the lead body 110, or are only slightly extended through the openings 184, as shown in FIG. 12A. Once the distal end 114 of the electrode lead 104 is positioned within the targeted tissue of the patient using an introducer or other conventional technique, the actuatable member 202 is rotated generally about the longitudinal axis 140 relative to the lead body 110 by the physician. The distal ends 136 of the one or more anchor wires are fed through the openings 184 of the lead body 110 responsive to the rotation of the actuatable member 202. Thus, the one or more anchor wires 132 move through the openings 184 of the lead body 110 and into the targeted tissue of the patient, as shown in FIG. 12B. This deployed position secures the position of the distal end 114 of the electrode lead 104 in the tissue of the patient. When it is desired to remove the electrode lead 104 from the patient, the anchor wires 132 may be retracted within the lumen 192 (FIG. 12A) to reduce damage to the tissue of the patient.

In one embodiment, a control member 204 may be used by the physician to move the actuatable member 194 (FIGS. 11A-B) along the longitudinal axis 140 relative to the lead body 110, or rotate the actuatable member 202 generally about the longitudinal axis 104 relative to the lead body 110. In one embodiment, the control member 204 is attached to the actuatable member and extends to a proximal end of the lead body 110 where it is accessible by the physician. The physician can slide the control member 204 along the longitudinal axis 140 relative to the lead body 110 to move the anchor 190 between the retracted (FIG. 11A) and deployed (FIG. 11B) positions. Similarly, the physician may rotate the control member 204 to move the anchor 200 between its retracted (FIG. 12A) and deployed (FIG. 12B) positions.

Figure 13:
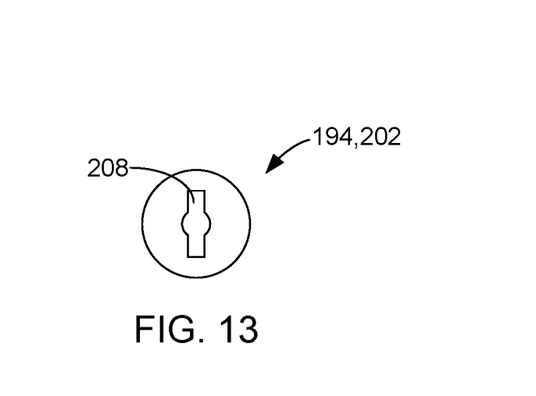
FIG. 13 is a simplified front view of an actuatable member in accordance with embodiments of the invention.

In one embodiment, the control member 204 has a distal end 206 that is removably attachable to the actuatable member 194 or 202. In one embodiment, the actuatable member 194 or 202 includes an aperture 208 that is configured to receive the distal end 206 of the control member 204. In one embodiment, the aperture 208 comprises a keyhole, as shown in the front view provided in FIG. 13. In one embodiment, the distal end 206 is configured to pass through or into the keyhole aperture 208 when angularly aligned with the keyhole aperture 208, and the distal end 206 of the control member 204 is prevented from passing through the keyhole aperture 208 when angularly misaligned with the keyhole aperture 208. This allows the physician to temporarily attach the distal end 206 to the actuatable member 194 or 202, move the actuatable member along the longitudinal axis 140 or rotate the actuatable member about the axis 140, and detach the control member 204 from the actuatable member so that it may be removed from within the lumen 192 of the lead body 110. Other configurations for the control member 204 and the actuatable member may also be used to provide this attachment function.

Figure 14:
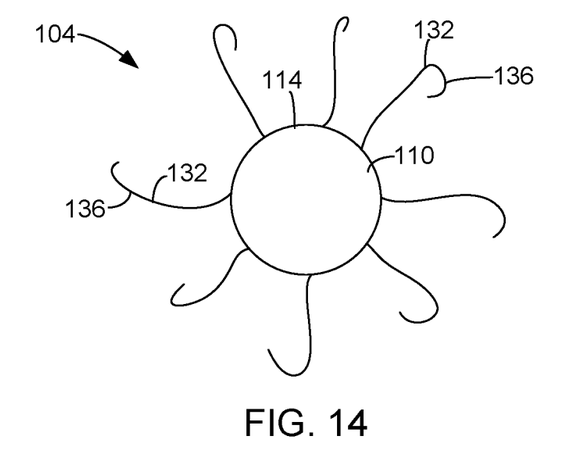
FIGS. 14 and 15 are simplified front views of an electrode lead formed in accordance with embodiments of the invention implanted in tissue of a patient.
Figure 15:
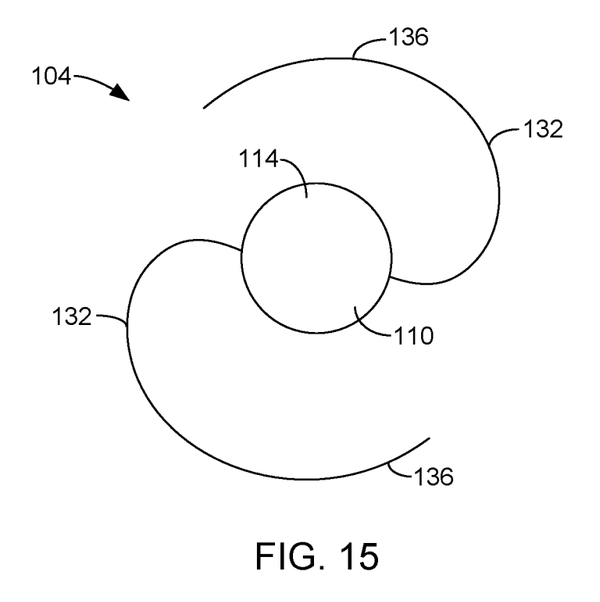

FIGS. 14 and 15 are front views of the distal end 114 of an electrode lead illustrating the deployment of anchor wires 132 in accordance with embodiments of the invention. The depicted anchor wires 132 may be components of anchors 130, 142, 180, 190 or 200, described above. In one embodiment, the anchor wires 132 at least initially extend in a radial direction from the lead body 110 relative to the longitudinal axis 140. In one embodiment, the plurality of anchor wires 132 are angularly displaced about the longitudinal axis. In one embodiment, the distal ends 136 of the anchor wires 132 are configured to coil in a plane that is approximately perpendicular to the longitudinal axis 140. In accordance with another embodiment, the anchor wires 132 are configured to coil in a plane that is approximately parallel to the longitudinal axis 140, as shown in FIG. 10C.

Figure 16:
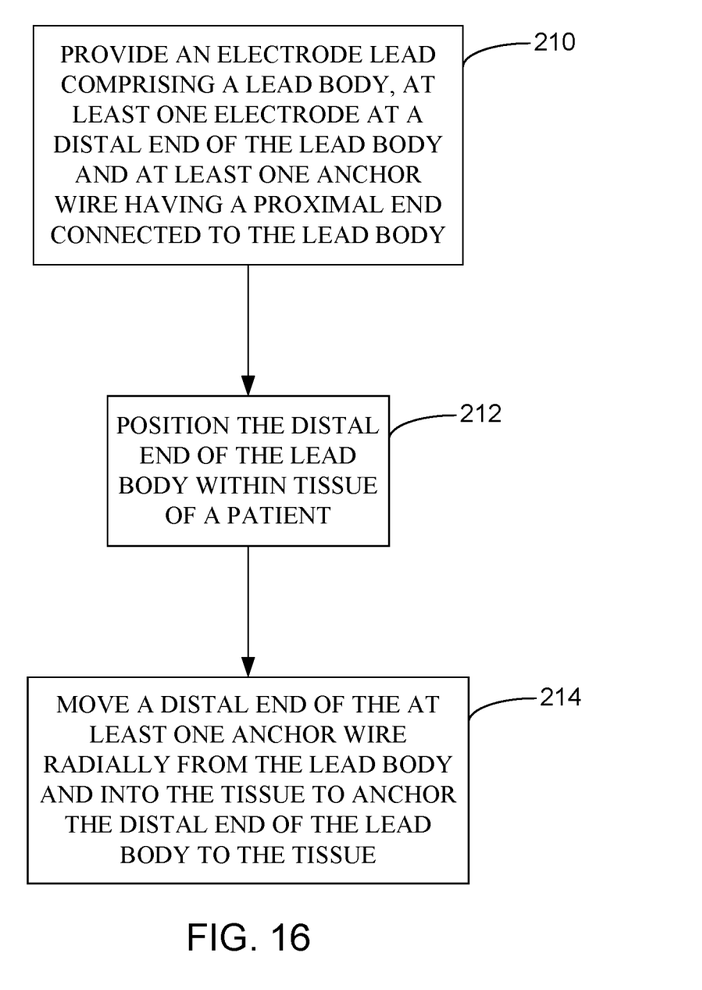
FIG. 16 is a flowchart illustrating a method in accordance with embodiments of the invention.

FIG. 16 is a flowchart illustrating a method in accordance with embodiments of the invention. At 210, an electrode lead 104 is provided comprising a lead body 110, at least one electrode 112 at a distal end 114 of the lead body 110, and at least one anchor wire 132 having a proximal end 134 connected to the lead body 110. In one embodiment, the proximal end 134 is considered to be connected to the lead body 110 through the connection to an actuatable member, such as actuatable member 194 or 202 located within a lumen 192 of the lead body 110, as shown in FIGS. 11A-B and 12A-B.

At 212, the distal end 114 of the lead body 110 is positioned within tissue of a patient. In one embodiment, the distal end 114 is positioned within tissue of the patient using an introducer, as described above. In one embodiment of step 212, an introducer sheath 162 is provided having a sheath wall 168 and a longitudinal axis 170. A distal end 164 of the introducer sheath 162 is then positioned in the targeted tissue of the patient. The distal end 114 of the lead body 110 is then fed into the introducer sheath 162 to position the distal end 114 proximate the distal end 164 of the introducer sheath 162 and the targeted tissue of the patient. In one embodiment, step 212 is performed while the at least one anchor wire 132 is in a retracted position.

At 214, a distal end 136 of the at least one anchor wire 132 is moved radially (i.e., relative to the longitudinal axis 140) from the lead body 110 and into the tissue to anchor the distal end 114 of the lead body 110 to the tissue. That is, the anchor comprising the at least one anchor wire 132 is moved from a retracted position to a deployed position in step 214.

In one embodiment of step 214, a proximal end 134 of the anchor wire 132 is attached to an actuatable member (194 or 202) within a lumen 192 of the lead body, as shown in FIGS. 11A-B and 12A-B. The actuatable member is then moved relative to the lead body 110. In one embodiment, the actuatable member is moved relative to the lead body 110 and the distal end 136 of the at least one anchor wire 132 is moved through an opening 184 in the lead body 110 responsive to moving the actuatable member. In one embodiment, the actuatable member (194) is moved along the longitudinal axis 140 relative to the lead body 110, as shown in FIGS. 11A-B. In accordance with another embodiment, the actuatable member (202) is rotated about the longitudinal axis 140 relative to the lead body 110, as shown in FIGS. 12A-B.

In one embodiment, the at least one anchor wire 132 is a component of anchor 130 (FIG. 2) or anchor 142 (FIG. 3). According to these embodiments, step 214 involves moving the lead body 110 relative to the introducer sheath 162 to deploy the at least one anchor wire 132 into the tissue of the patient. The introducer sheath 162 may then be removed from the tissue without disturbing the deployed anchor wire 132.

When the at least one anchor wire 132 is held in a compressed state by the introducer sheath 162 during the positioning step 212, step 214 of the method is performed by removing the introducer sheath from the tissue. This allows the compressed anchor wire 132 to expand toward its quiescent expanded state and into the tissue of the patient.

Although the present invention has been described with reference to preferred embodiments, workers skilled in the art will recognize that changes may be made in form and detail without departing from the spirit and scope of the invention.

What is claimed is:

1. A system comprising:
   an introducer including a sheath and a removable needle guide, the sheath having a sheath wall and a longitudinal axis, the sheath including a distal end portion and a proximal end portion, the distal end portion defining at least one opening through the sheath wall;
   an electrode lead including a lead body and at least one electrode at a distal end portion of the lead body, the distal end portion of the lead body configured to be received within the sheath, the lead body configured to move relative to the sheath; and
   an anchor wire including a proximal end portion and a distal end portion, the proximal end portion of the anchor wire being coupled to the distal end portion of the lead body, the anchor wire being disposed within the sheath when the anchor wire is in a retracted position, the anchor wire configured to move to a deployed position in which at least the distal end portion of the anchor wire is disposed outside of the sheath in response to movement of the lead body relative to the sheath, wherein, in response to the anchor wire moving from the retracted position to the deployed position, the distal end portion of the anchor wire moves through the at least one opening in the sheath wall.

2. The system of claim 1, wherein the removable needle guide is configured to be removed from the sheath after the sheath is disposed within a body of a patient.

3. The system of claim 1, wherein the distal end portion of the anchor wire is configured to move through the at least one opening in the sheath wall responsive to rotation of the lead body about the longitudinal axis relative to the sheath.

4. The system of claim 1, further comprising:
   a control unit coupled to a proximal end portion of the lead body, the control unit including circuitry configured to process electrical signals received from the at least one electrode.

5. The system of claim 1, wherein the anchor wire includes a memory shaped material.

6. The system of claim 1, wherein the at least one opening includes a first opening through the sheath wall and a second opening through the sheath wall, and the anchor wire is a first anchor wire, the system further comprising:
   a second anchor wire having a proximal end portion coupled to the distal end portion of the lead body,
   wherein, in response to movement of the lead body relative to the sheath, the first anchor wire is configured to move through the first opening in the sheath wall, and the second anchor is configured to move through the second opening in the sheath wall.

7. The system of claim 6, wherein the second anchor wire is displaced from the first anchor wire along a longitudinal axis of the lead body.

8. The system of claim 6, wherein the second anchor wire is angularly displaced from the first anchor wire about a longitudinal axis of the lead body.

9. The system of claim 1, wherein the introducer includes a handle, the handle being coupled to a proximal end portion of the removable needle guide.

10. The system of claim 1, wherein the sheath is configured to be split into separate halves to allow for removal of the sheath from a body of a patient.

11. The system of claim 1, wherein the distal end portion of the lead body includes an actuatable member disposed within a lumen of the lead body, wherein the actuatable member is coupled to the proximal end portion of the anchor wire.

12. The system of claim 11, wherein the actuatable member is configured to move relative to the lead body along a longitudinal axis of the lead body.

* * * * *